(12) United States Patent
Roeher et al.

(10) Patent No.: US 7,775,986 B2
(45) Date of Patent: Aug. 17, 2010

(54) THERAPY DEVICE WITH A TIME-VARIABLE BLOOD REGULATION

(75) Inventors: Otfried Roeher, Dresden (DE); Steffen Korth, Elleben (DE)

(73) Assignee: B. Braun Medizintechnologie GmbH, Melsungen (DE)

( * ) Notice: Subject to any disclaimer, the term of this patent is extended or adjusted under 35 U.S.C. 154(b) by 476 days.

(21) Appl. No.: 11/786,261

(22) Filed: Apr. 10, 2007

(65) Prior Publication Data

US 2009/0112102 A1    Apr. 30, 2009

(51) Int. Cl.
*A61B 5/02* (2006.01)
(52) U.S. Cl. .................. 600/485; 600/483; 600/504
(58) Field of Classification Search .......... 600/485, 600/483, 504
See application file for complete search history.

(56) References Cited

U.S. PATENT DOCUMENTS 5,099,852 A * 3/1992 Meister et al. ............ 600/485
5,503,624 A * 4/1996 Roeher et al. ............. 604/65
2002/0107449 A1 * 8/2002 Roeher .................... 600/485

FOREIGN PATENT DOCUMENTS

EP    0 956 872 A2    11/1999
EP    1 226 838 A2    7/2002

* cited by examiner

*Primary Examiner*—Robert L Nasser
*Assistant Examiner*—Michael D'Angelo
(74) *Attorney, Agent, or Firm*—RatnerPrestia

(57) ABSTRACT

A therapy device having a blood pressure device and a regulating device for a time-variable regulation of the blood pressure, which decides, during a therapy procedure, dependent on detected blood pressure value, whether the blood regulation is continued with hypothetical or with real blood pressure values. The regulating device processes various categories of blood pressure values, i.e. blood pressure values obtained by the regulating device according to an implemented time schedule, blood pressure values requested by measurement and evaluation device, and blood pressure values requested by medical staff. Besides the regular triggers (RT) generated at regular intervals, the irregular triggers (IRT) and the quasi-regular triggers (QRT) requested externally at respective times are also evaluated.

3 Claims, 4 Drawing Sheets

THERAPY DEVICE WITH A TIME-VARIABLE BLOOD REGULATION

BACKGROUND OF INVENTION

Figure 1:
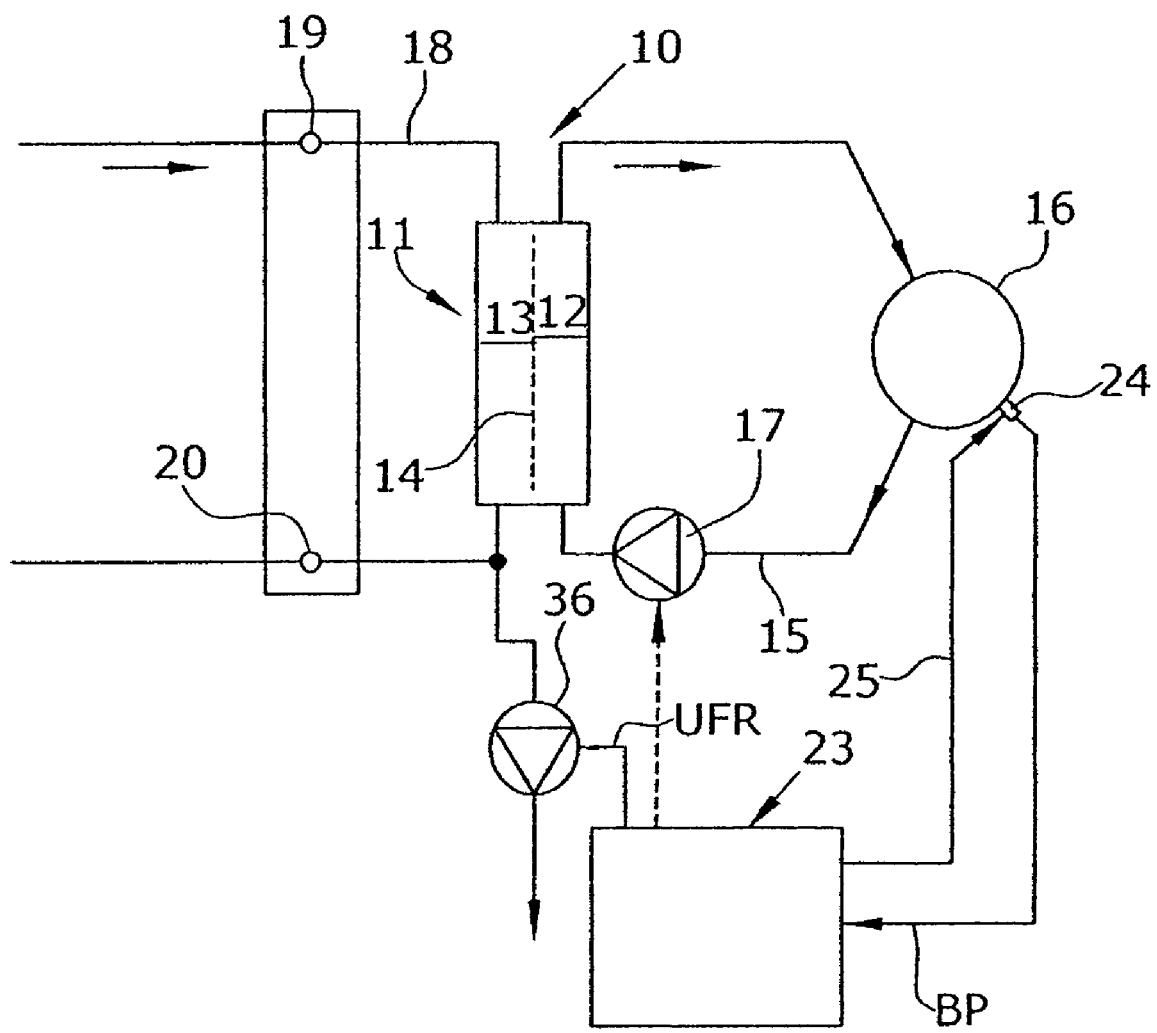

The invention refers to a therapy device comprising a blood pressure measurement device and a regulating means with a time-variable regulation of the blood pressure of a patient during a therapy procedure, in particular to a therapy device for extracorporeal blood purification.

In various therapies, e.g. in hemodialysis, it is necessary to constantly monitor the blood pressure of a patient. To this end, apparatus for a non-invasive measurement of the blood pressure are used that comprise a sleeve to be placed around an arm of a patient, are inflated and then slowly relaxed while measuring the pressure. To achieve a quasi-continuous blood pressure regulation, the regulating means has to perform regulating operations at intervals of a few minutes. The number of blood pressure measurements required for this purpose during a treatment of several hours can be reduced substantially if, at defined moments, the blood pressure measurements are substituted with blood pressure values obtained from previous treatments of the same patient.

European Patent Application EP 1 226 838 A2 describes therapy devices with an interval-like blood pressure measurement and with a reduced number of measurements. Based on the equal length of all intervals, e.g. 5 minutes per interval, the regulating means guarantees an evaluation of the blood pressure profile and the blood pressure trends in each interval according to uniform rules, as described in EP 0 956 872 B1.

Since multifactorial causes have to be considered with respect to morbid events during hemodialysis, such as hypotension, vertiginous attacks, vomiting and the like, monitors for other parameters (e.g. ECG, relative volume of blood, hematocrit, amount of oxygen contained in the blood) are sometimes used in clinical practice to detect complications. Depending on the measurement results, this may lead to requirements for additional blood pressure measurements. Clinical experience with dialysis patients show that, depending on the condition of the patient, sometimes also the medical staff is required to take blood pressure measurements directly.

It is thus an object of the invention to arrange a therapy device with a reduced number of blood pressure measurements such that a time-variable blood pressure control is possible.

SUMMARY OF INVENTION

According to the invention, after a blood pressure measurement, a regulating means decides in dependence on the blood pressure value obtained, whether the blood pressure regulation is continued on the basis of hypothetical or real blood pressure values. To this end, the regulating means includes the following categories of blood pressure values in the regulation of the blood pressure:

a) blood pressure values called by the regulating means, or substituted with values of previous therapy procedures, at defined times according to an implemented time schedule in dependence on the target parameters of the treatment set at the therapy device (e.g. total volume of ultrafiltration, duration of treatment, maximum ultrafiltration rate), b) blood pressure values called by connected external measurement and evaluation devices for other physiological parameters (e.g. ECG, relative blood volume, hematocrit, amount of oxygen contained in the blood) at other times than under a) by irregular triggers (IRT) and/or quasi-regular triggers (ORT), and c) blood pressure values called manually by medical staff at other times than under a) and b) by irregular triggers (IRT) and/or quasi-irregular triggers (QRT).

Preferably, the regulating means performs the following steps:

A controlling the blood pressure measurement device to perform interval-like blood pressure measurements, B obtaining and time-dependent evaluation of all further blood pressure measurements requested by connected external devices and/or medical staff, C establishing and storing an archive of the time-dependent courses of the blood pressure for a plurality of therapy procedures, D regulating the blood pressure using measured blood pressure values and substitution values of previous therapy procedures in form of a template.

In a preferred embodiment, it is provided that the blood pressure measurements requested by external connected devices or by medical staff are evaluated differently depending on their timing in the regulation intervals defined by the regulating means. An externally requested blood pressure measurement taken a short time, e.g. 60 sec, before a new regulation interval is equated to a regular blood pressure measurement as it would be caused by the regulating means itself at the times set therefor, without an external request, in response to a regular trigger (RT). The externally initiated trigger is therefore considered a quasi-regular trigger (QRT). Other externally requested blood pressure measurements effected at a larger time interval, e.g. >60 sec. before the start of a new regulation interval, are detected by the regulating means as irregular triggers (IRT) and are evaluated on a separate regulation base that considers the points in time within the respective regulation interval. With a plurality of external requests within a regulation interval, this regulation base promptly reacts to each individual request by adjusting the set value of the blood pressure regulation, e.g. the ultrafiltration rate. Independent of the number of external requests and in the same manner as for regular blood pressure values, the reference value used therefore is the respective value of the set value which the regulating means has obtained at the beginning of the respective regulation interval. As soon as an externally requested blood pressure measurement leads to a blood pressure value within the blood pressure range requiring regulation, the regulating means itself causes a further measurement of the blood pressure at the beginning of the next regulation interval. Even without an external request, this blood pressure measurement is repeated in the following regulation intervals in the same manner as after regular measurements, until the blood pressure is again above the blood pressure range requiring regulation. By the operation described above, the regulating means guarantees a time-variable blood pressure regulation that, independent of the time and the number of external requests, reacts promptly after each blood pressure measurement and thus enhances the quality of the blood pressure regulation and the safety of a patient, even in critical situations. At the same time, unnecessary measurements at the patient are avoided, when external and regular requests for blood pressure measurements follow each other in a small time interval.

The invention is particularly suited for dialysis devices and other apparatus for extracorporeal blood treatment, but also for infusion therapy, for example.

DETAILED DESCRIPTION OF THE INVENTION

The following is a detailed description of an embodiment of the invention with reference to the drawings.

Figure 2:
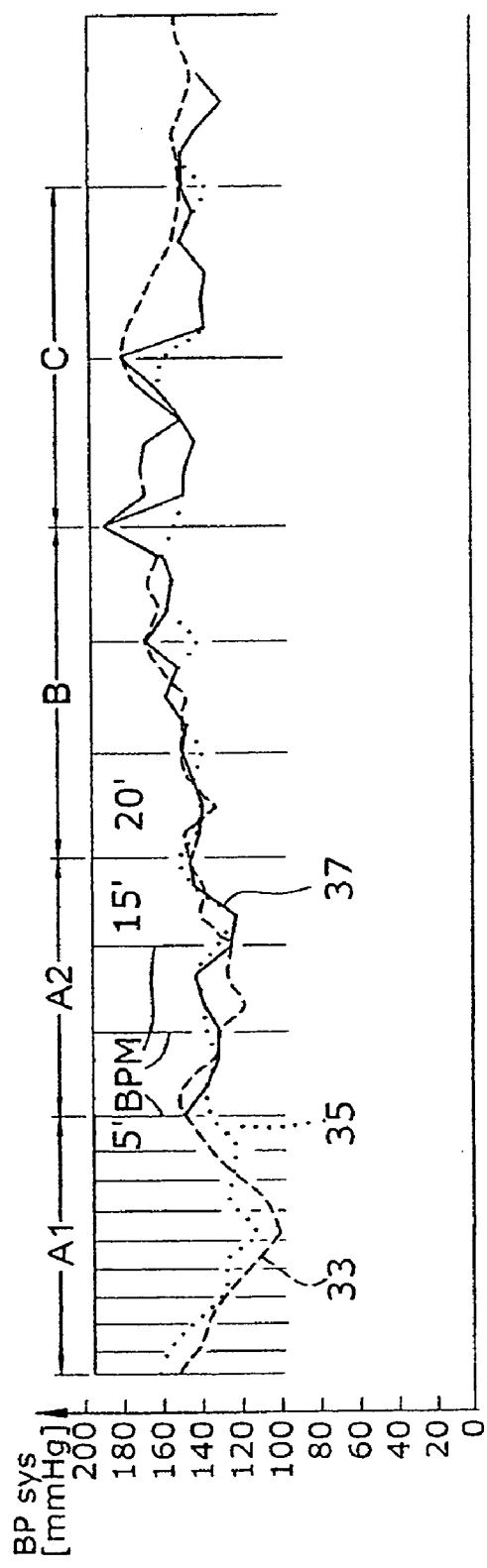
Figure 2:
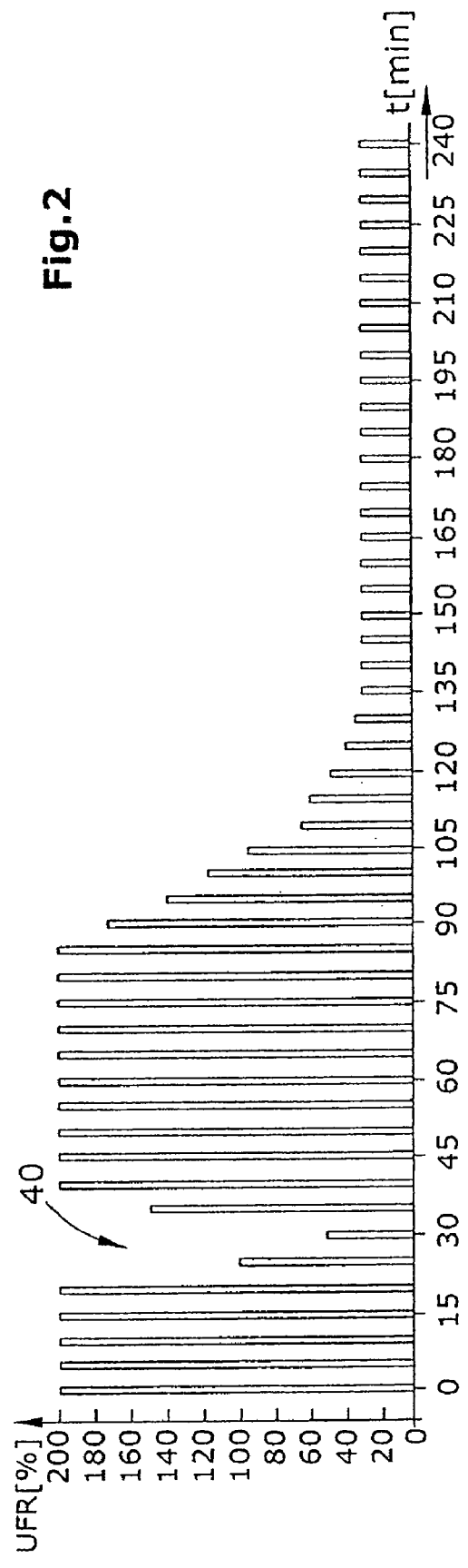
Figure 3:
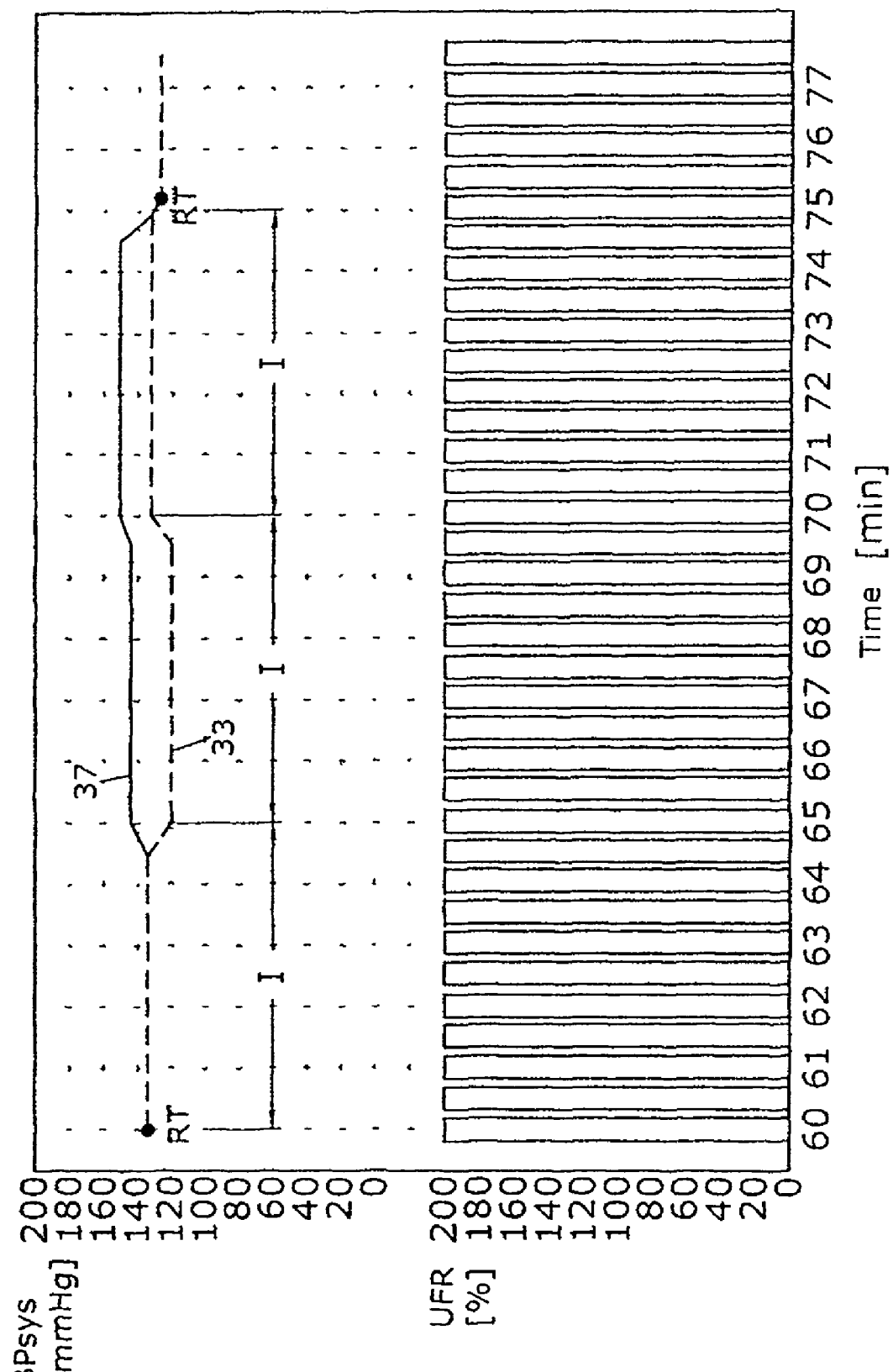
Figure 4:
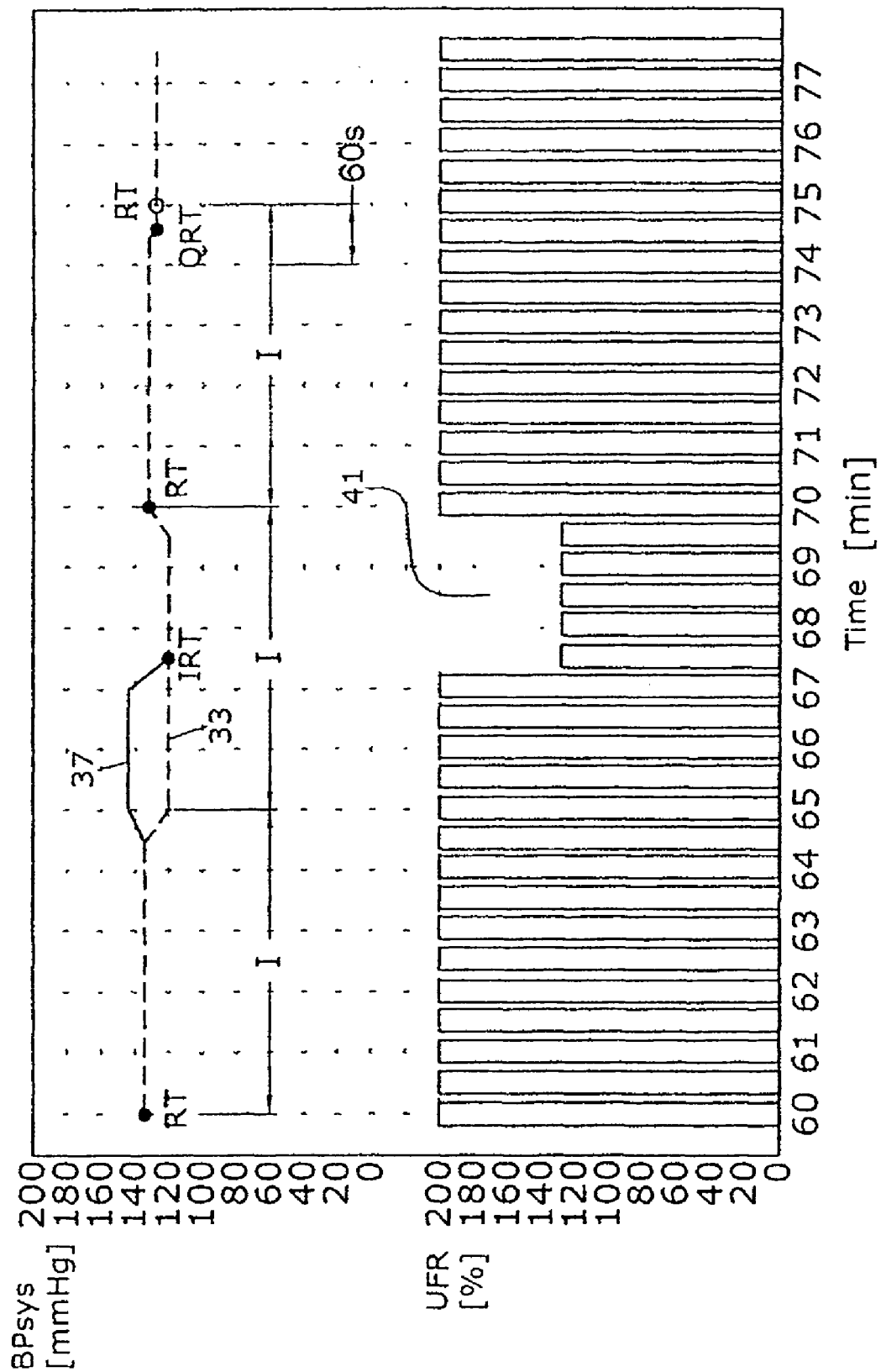

In the figures:

FIG. 1. is a schematic illustration of a therapy device in the form of a dialysis device, FIG. 2 is a time chart of the dialysis treatment representing the blood pressure and the ultrafiltration rate, FIG. 3 is a time chart with a regular response by the regulating means without external requests for measurement, and FIG. 4 is a time chart with a time-variable response by the regulating means upon external requests.

The general structure of the dialysis device shown in FIG. 1 corresponds to that of EP 0 956 872 B1 or EP 1 226 838 A2. The dialysis device 10 comprises an ultrafiltration device 11 with a primary chamber 12 and a secondary chamber 13 separated by a membrane 14. The primary chamber 12 is part of a blood circuit 15, wherein blood taken through the arterial system of the patient is purified by the ultrafiltration device 11 and is then returned to the patient 16 through the venous system. A pump 17 is provided in the blood circuit 15. The pump is configured as a volumetric pump, i.e. the delivery rate of this pump corresponds to its drive speed, and it is controllable.

The secondary chamber 13 of the ultrafiltration device 11 is situated in the path 18 of the hemodialysis solution in which hemodialysis solution is pumped. The hemodialysis solution is fed from a reservoir (not illustrated), absorbs additional substances from the blood in the ultrafiltration device 11 and is then pumped to an outlet (not illustrated). Upstream and downstream of the secondary chamber 13 a respective flow-through chamber 19, 20 is arranged in the path of the dialysis liquid, which regulates the flow rate at the respective location. The flow-through chamber 19 and the flow-through chamber 20 have the same delivery rate. Through the volume-controlled ultrafiltration pump 36, the desired ultrafiltration volume UFV is withdrawn at a defined ultrafiltration rate UFR. The time integral over the ultrafiltration rate UFR gives the ultrafiltration volume UFV, that is the liquid volume that has passed the membrane 14 since the start of the treatment. The ultrafiltration rate is regulated by the regulating means 23 which supplies control signals for the delivery rate of the pump 36. The delivery rate of the pump is set such that a desired ultrafiltration rate is obtained.

The regulating means 23 further receives the blood pressure signal BP from a blood pressure meter 24 attached to the body of a patient. The blood pressure meter comprises an inflatable sleeve placed around a patient's arm, and performs non-invasive blood pressure measurements. The times of the blood pressure measurement are defined internally by the regulating means 23 via the lines 25 and externally by connected monitors and/or the medical staff. Besides the blood pressure value, the regulating means 23 may also be supplied with blood pressure trend values as described in EP 0 956 872 B1. The regulating means 23 regulates the ultrafiltration rate UFR as a function of the input values received.

FIG. 2 illustrates an example of the blood pressure regulation as it is regulated by the regulating means 23 in the absence of external requests for additional blood pressure measurements during a therapy procedure.

The lower half of FIG. 2 illustrates the course in time of the relative ultrafiltration rate (in %). During this dialysis treatment, first, a relatively high ultrafiltration rate of 200% is used, the ultrafiltration rate subsequently being lowered to a minimum value of about 25%.

In the upper half of FIG. 2, the systolic blood pressure Bpsys of a patient during this dialysis treatment is plotted. Here, the dashed line represents the current course 33 of the blood pressure, as it would result from a continuous measurement of the blood pressure.

In the regulating means 23 or in a central computer, an archive of the courses in time of the blood pressure in previous therapy procedures is stored.

In an initial phase A1, the current blood pressure is measured by the blood pressure measuring device 24 at intervals of 5 min and stored as the profile 33 of the blood pressure. The blood pressure regulation is effected exclusively in dependence on the current blood pressure profile 33. In the present embodiment, the initial phase lasts 45 min. At the end of the initial phase A1, the current blood pressure profile 33 is compared to the stored blood pressure profiles of previous treatments of the same patient. Using statistical analyses (average values, standard deviations, t-test or image processing methods), the blood pressure profile with the greatest similarity to current blood pressure profile is obtained from the data memory and used as the (dotted) template 35 for the treatment underway.

In the following second phase A2, blood pressure measurements, represented by the lines BPM, are performed according to the schedule of the regulating means 23, i.e., in the present case, at intervals of 15 min. In the phase B, the blood pressure measurements BPM are take at intervals of 20 min. or, in the final phase C, at intervals of 30 min. However, the blood pressure regulation still takes place at intervals of 5 min., wherein at the respective times when no measurement is taken, the values of the (dotted) template are taken as the actual value of the blood pressure, whereas at the times of blood pressure measurement BPM, the current values of the (dashed) blood pressure profile 33 are used. The values used as the actual blood pressure in the regulation are evident from the solid curve 37 representing the "hypothetical blood pressure profile".

From FIG. 2 it is apparent that at the times of blood pressure measurement BPM the hypothetical blood pressure profile that is relevant for the regulation assumes the value of the current (dashed) blood pressure 33, whereas at the intermediate times, the value of the (dotted) template is assumed.

When the actual value falls below a predetermined limit value, 130 mmHg in the present embodiment, the ultrafiltration rate UFR is reduced, as indicated in the region 40 in FIG. 2. By reducing the ultrafiltration rate, less liquid is withdrawn from the patient, whereby a decrease in blood pressure is counteracted.

For the treatment section from 60 min to 77 min in FIG. 2, FIG. 3 and FIG. 4 illustrate, over a spread time axis, the time-variable response of the regulating means 23 to externally requested blood pressure measurements. The regulating means causes a splitting of the time axis into intervals I of 5 min in this case and respectively lasting from 60-65 min, from 65-70 min and from 70-75 min, and so on. In the absence of external requests (FIG. 3), the regulating means 23, in the treatment phase A2, causes measurements only every 15 min, i.e. after 3 intervals, respectively, by the regular triggers RT at the times 60 min and 75 min according to criterion a). In the first interval from 60-65 min following a regular trigger RT, the blood pressure regulation is performed on the basis of the measured values 33. In the second and third intervals I from 65 min to 70 min and from 70 min to 75 min, the blood pressure regulation is performed using the hypothetical values 37.

During the first interval of each period, the measured blood pressure value 33 is taken as the basis of the regulation. In the subsequent time intervals of the same period, the regulation is effected using the curve 37 that indicates the "hypothetical blood pressure profile". Thus, frequent blood pressure measurements are avoided. If, however, according to FIG. 4, an irregular trigger IRT occurs during the use of curve 37, the regulation may return to the current curve 33. Thus, the irregular trigger ITR initiates a new blood pressure measurement, which has the consequence that at the time 70 min, i.e. at the beginning of the third interval I, a blood pressure measurement is taken again.

The time-variable response of the regulating means in dependence on the times of external requests is illustrated in FIG. 4. The plotted external request corresponding to category b) or c) at the time 67.5 min initiates an irregular trigger IRT since the time of request lies outside the tolerance period of 60 sec before the start of the next 5 min interval at 70 min. The regulating means responds promptly by decreasing the ultrafiltration rate UFR in the time period 41, since the blood pressure measured is <130 mmHg and is within the blood pressure range requiring regulation. When the ultrafiltration rate is decreased, the regular triggers RT are generated at shorter intervals, here at offsets of one interval I. Thus, the regulating means 23 causes a regular trigger RT already at the beginning of the next 5 min interval I at 70 min, thereby also causing another regular blood pressure measurement. Since the measured value then is >130 mmHg, the regulating means 23 now increases the relative ultrafiltration rate UFR to 200% again. The plotted external measurement request at 74.5 generates a quasi-irregular trigger QRT, since, here, the time of request is within the tolerance period of 60 sec before the start of the next 5 min interval I. The otherwise due regular trigger at 75 min is therefore suppressed and the blood pressure value=130 mmHg determined by the quasi-irregular trigger QRT is taken over for the next 5 min interval from 75 min to 80 min. In this example, the hypothetical values 37 become effective only in the period from 65.0 min to 67.5 min. In the periods from 60.0 min to 65.0 min and from 67.5 min to 80.0 min, the regulation is effected using the current blood pressure profile 33.

The invention claimed is:

1. A therapy device for a treatment with settable target parameters, such as total ultrafiltration volume, treatment duration, maximum ultrafiltration rate, comprising a blood pressure device (24) and a regulating means (23) for a time-variable regulation of the blood pressure of a patient during a therapy procedure in dependence on detected blood pressure values, the regulating means deciding after each blood pressure measurement, in dependence on the blood pressure value detected, whether the blood regulation is continued with previously stored values or with real blood pressure values, and wherein the regulating means includes the following categories of blood pressure values in the regulation of the blood pressure:

a) blood pressure values requested by the regulating means, or substituted with values of previous therapy procedures, at defined times according to an implemented time schedule in dependence on the target parameters of the treatment set at the therapy device, b) blood pressure values requested by measurement and evaluation devices for other physiological parameters at other times than under a) by irregular triggers (IRT) and/or quasi-regular triggers (QRT), and c) blood pressure values requested manually by medical staff at other times than under a) and b) by irregular triggers (IRT) and/or irregular triggers (QRT): and wherein the regulation means (23) performs the following steps:

A acquiring, classifying and processing all blood pressure values obtained according to the categories a) to c), in dependence on the respective times of the measurements and corresponding to the respective times of the measurements and corresponding to the schedule for the blood pressure regulation predefined by the regulating means (23), B substituting all blood pressure values of category a) with the obtained blood pressure values of categories b) and c), if these measurement values are transferred from the blood pressure meter to the regulating means within a predetermined tolerance period immediately before the times defined for the blood pressure values of category a), C establishing and storing an archive of the time profiles of the blood pressure in case of a plurality of therapy procedures, D obtaining as a template (35) the blood pressure profile among the stored profiles that is most similar to the current blood pressure profile (33), E regulating the blood pressure using the blood pressure values of categories a) to c), the values for scheduled times without blood pressure measurement being taken from the template (35).

2. The therapy device of claim 1, wherein after each measurement the current blood pressure profile is checked again for similarity to the stored blood pressure profiles.

3. The therapy device of claim 1, wherein the regulation means (23) further performs the following step:

suppressing the next blood pressure measurement to be requested by the regulating means according to the implemented time schedule if the measurement values for the obtained blood pressure values of categories b) or c) are transferred to the regulating means within the predetermined tolerance period immediately before the times defined for the blood pressure values of category a).

* * * * *